(12) United States Patent
You et al.

(10) Patent No.: US 8,603,311 B2
(45) Date of Patent: Dec. 10, 2013

(54) DEVICE FOR MEASURING PH AT TEMPERATURE

(75) Inventors: Dominique You, Verrieres le Buisson (FR); Edmond Blanchard, Bretigney S/Orge (FR)

(73) Assignee: Commissariat à l'Energie Atomique et aux Energies Alternatives (FR)

(*) Notice: Subject to any disclaimer, the term of this patent is extended or adjusted under 35 U.S.C. 154(b) by 0 days.

(21) Appl. No.: 13/280,894

(22) Filed: Oct. 25, 2011

(65) Prior Publication Data

US 2012/0125769 A1 May 24, 2012

(30) Foreign Application Priority Data

Oct. 25, 2010 (FR) .................................. 10 58752

(51) Int. Cl.
*G01N 27/333* (2006.01)
*G01N 27/49* (2006.01)

(52) U.S. Cl.
USPC ......... 204/408; 204/416; 205/787.5; 324/438

(58) Field of Classification Search
USPC .......... 204/400–403.02, 403.06, 403.07, 408, 204/412, 416, 418–420; 205/775, 775.5, 205/777.5–782.5, 786–788, 792, 793, 205/794.5; 324/438
See application file for complete search history.

(56) References Cited

U.S. PATENT DOCUMENTS

| | | | | |
|---|---|---|---|---|
| 3,839,162 A | * | 10/1974 | Ammer | 205/781.5 |
| 4,240,879 A | | 12/1980 | Dobson | |
| 4,966,670 A | * | 10/1990 | Calzi | 204/406 |
| 2005/0214464 A1 | * | 9/2005 | Moriyoshi et al. | 427/307 |
| 2006/0044554 A1 | * | 3/2006 | Mertz et al. | 356/246 |

FOREIGN PATENT DOCUMENTS

| | | |
|---|---|---|
| GB | 2044464 A | 10/1980 |
| JP | 62266200 A * | 11/1987 |

OTHER PUBLICATIONS

JP62266200A, Matsunaga 1987, english equivalent of the abstract.*
Search Report from French Application No. 743449 dated Jun. 15, 2011.
Zhang R.H . et al . : "Zr /Zr02 sensors for in situ measurement of pH in high-temperature and -pressure aqueous solutions" , Analytical Chemistry, vol. 80 , No. 8 , (Apr. 15, 2008) , pp. 2982-2987, XP055000630.

* cited by examiner

*Primary Examiner* — Susan D Leong
(74) *Attorney, Agent, or Firm* — Lerner, David, Littenberg, Krumholz & Mentlik, LLP

(57) ABSTRACT

The invention relates to a pH measuring device containing a reference cell which includes a tank filled with an electrolyte solution and a platinized platinum reference electrode immersed in the tank. The measuring device also contains a measuring cell. The measuring cell contains a platinized platinum measuring electrode which is immersed in the solution to be measured. The measuring device also contains a temperature regulator to ensure that the temperature is the same in the reference cell as in the measuring cell. The measuring device also contains a particle pressure regulator to ensure that the hydrogen partial pressure is the same in the reference cell as in the measuring cell and a fluid pressure regulator to ensure that the pressure is the same in the reference cell as in the measuring cell.

8 Claims, 3 Drawing Sheets

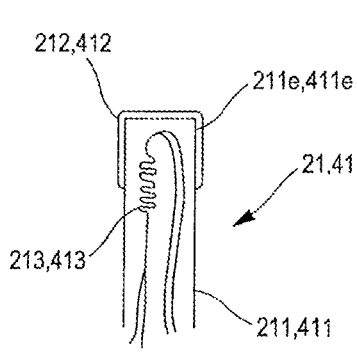
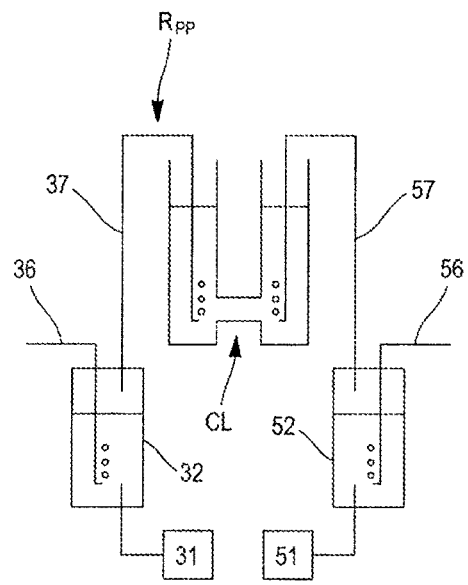
FIG. 2
FIG. 4
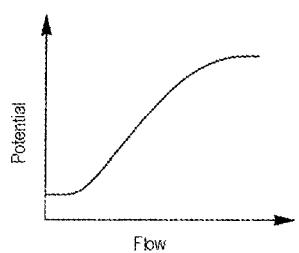
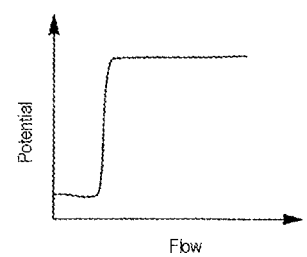
FIG. 3a
FIG. 3b

DEVICE FOR MEASURING PH AT TEMPERATURE

CROSS-REFERENCE TO RELATED APPLICATIONS

This application claims the benefit of French Patent Application No. 1058752 filed Oct. 25, 2010, entitled DEVICE FOR MEASURING PH AT TEMPERATURE, the disclosure of which is hereby incorporated herein by reference.

TECHNICAL FIELD

The invention relates to the technical field of measuring the pH of a solution. More particularly, the invention concerns the field of pH measuring devices throughout the ambit of liquid water stability, for example, for a nuclear plant.

TECHNOLOGICAL BACKGROUND

The pH measures the activity of hydrogen ions $H^+$ in solution, especially in aqueous solution where these ions form oxonium ions $H_3O^+$ (also called hydronium) with water. The pH reflects the acidity of the solution. For example, in an aqueous medium at 25° C., a pH of 7 is called neutral, a pH above 7 is called basic and a pH below 7 is called acidic.

Since acidity is a parameter to consider in metal corrosion mechanisms, and especially in metal ducts for industrial plants, knowing the pH enables to control corrosion of these ducts.

Acidity is also a parameter to consider in the solubility of chemical species in aqueous solution. Therefore, knowing the pH enables to control deposition of chemical compounds on surfaces due to crystallization of these compounds at certain pHs. Thus, it is possible, for example, to prevent fouling of surfaces and clogging of steam generators.

Finally, certain industrial procedures require operation in a limited pH range and therefore require measuring the pH.

The most widely used pH measuring devices are based on a glass membrane. These measuring devices only work at temperatures below 100° C.

Other measuring devices can work up to 280° C. These devices couple a reference Ag/AgCl electrode with a polymer electrode body, on the one hand, with a platinum electrode immersed in the solution whose pH is to be measured, on the other hand. The thermal stability of the AgCl salt and the melting temperatures of the polymers used to fabricate the electrode body require a limit of operative temperature of 280° C. Furthermore, the possible presence of chloride can damage iron-based metal circuits and that of silver is extremely harmful for nuclear circuits.

There are devices for measuring above 280° C. For example, yttrium-zirconium oxide membrane devices work above 300° C. However, they do not enable to go below 300° C. because diffusion of oxygen into the oxide decreases exponentially with temperature. The diffusion of oxygen is insufficient to make reliable measurements below around 300° C. These measuring devices also do not measure the activity of the hydronium ions of the solution, but rather the partial pressure of oxygen.

PRESENTATION

One objective of the invention is to overcome at least one of the drawbacks of the prior art presented above.

In this aim, the invention provides a measuring device for measuring the pH of a solution being measured comprising:

a reference cell including:
a tank filled with an electrolyte solution;
a platinized platinum reference electrode immersed in the tank;
a measuring cell including:
a platinized platinum measuring electrode to be immersed in the solution being measured;
characterized in that the measuring device also comprises:
a temperature regulator to ensure the same temperature in the reference cell and the measuring cell;
a partial pressure regulator to ensure the same hydrogen partial pressure in the reference cell and the measuring cell; and
a fluid pressure regulator to ensure the same pressure in the reference cell and the measuring cell;

One advantage of this measuring device is that the usable temperature range is not limited to below 280° C. while allowing direct measurement of the activity of hydronium ions.

Other optional and non-limiting features are:
the temperature regulator has a reference thermometer immersed in the electrolyte solution, a measuring thermometer to be placed in contact with the solution being measured, and a temperature comparator to compare the temperatures measured by the reference and measuring thermometers;
the temperature regulator also has at least one heater to heat the electrolyte solution or solution being measured according to the result of the comparison performed by the temperature comparator;
the measuring device also has a hydrogen gas inlet in the electrolyte solution and a hydrogen gas inlet in the solution being measured;
the partial pressure regulator has a valve positioned on each of the hydrogen gas inlets so as to open when the hydrogen partial pressure in the electrolyte solution, respectively the solution being measured, is below a set partial pressure;
the partial pressure regulator also has a comparator, for each of the valves, to compare the hydrogen partial pressure in the electrolyte solution, respectively the solution being measured, to the set partial pressure and to control the opening of the valve according to the result of the comparison;
the fluid pressure regulator has a reference manometer, a measuring manometer, an outlet valve and a fluid pressure comparator to compare the fluid pressure of the tank to that of the solution and to consequently control the outlet valve; and
the measuring device also has an ionic strength regulator to ensure the same ionic strength in the reference cell and the measuring cell;

PRESENTATION OF THE DRAWINGS

Other objectives, features and advantages will appear upon reading the detailed description that follows in reference to the drawings given by way of illustration and non-limiting, among which:

FIG. 1 schematically illustrates one example of embodiment of the pH measuring device according to the invention;

FIG. 2 schematically illustrates a platinized platinum electrode used in the measuring device of FIG. 1;

FIGS. 3a and 3b show the influence of flow on the potential measured by a platinum electrode, respectively when the electrode is not platinized and when the electrode is platinized;

FIG. 4 shows one example of embodiment of a partial pressure regulator used in the measuring device of FIG. 1.

DETAILED DESCRIPTION

In the following description, thermometer means any device for measuring temperature and manometer means any device for measuring pressure.

pH Measuring Device

Figure 1:
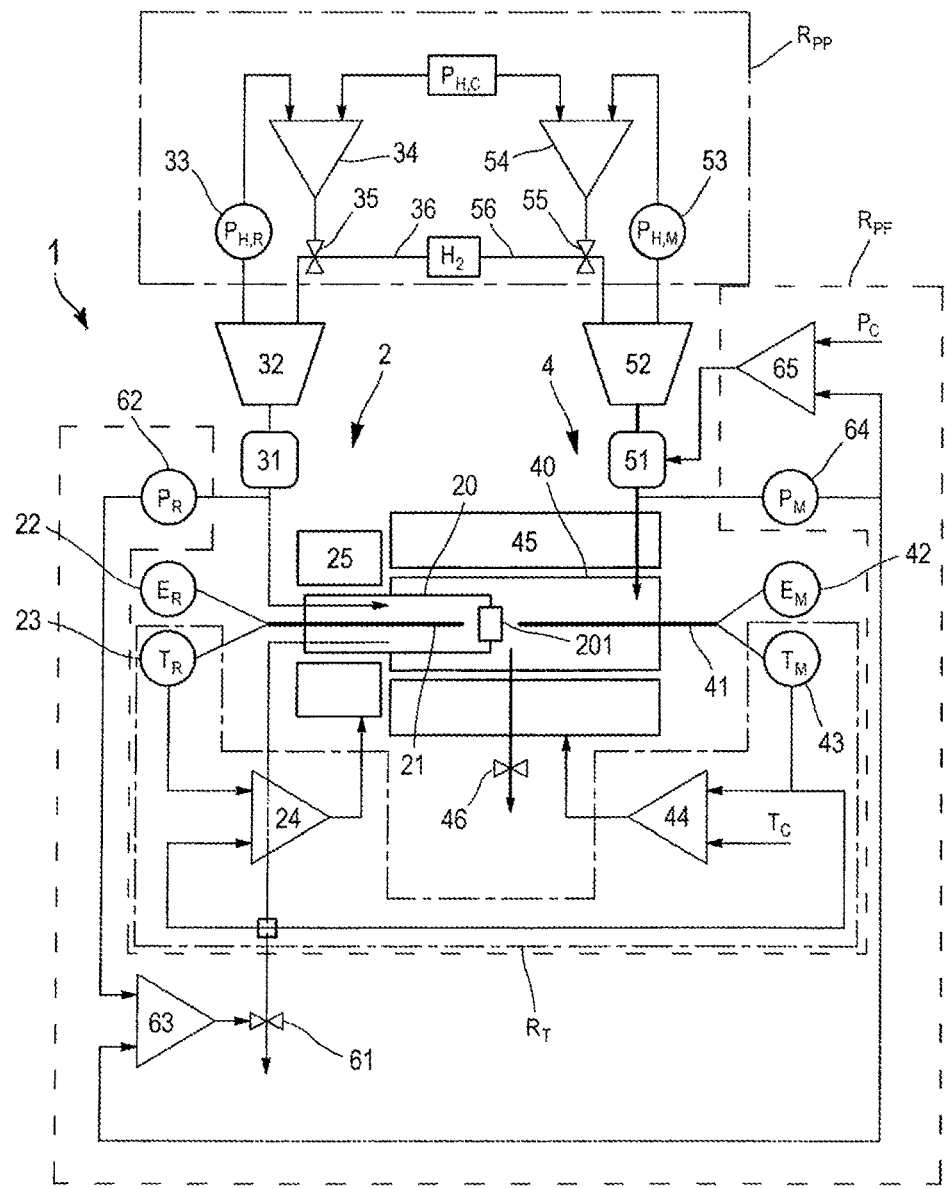

In reference to FIG. 1, a pH measuring device for a solution being measured whose pH one wishes to know is described in detail below.

The measuring device 1 comprises a reference cell 2 and a measuring cell 4.

The reference cell 2 has a reference electrode 21 and a tank 20 filled with an electrolyte solution, in which the reference electrode 21 is immersed. The tank 20 has a sintered filter 201 at its end made of insulating microporous oxide that enables hydrogen ions to pass from the electrolyte solution inside the tank to the solution being measured and vice versa.

The sintered filter 201 can have pores whose size is from 15 kDa to 1500 kDa. The materials that can be used are zirconium dioxide ($ZrO_2$), titanium dioxide ($TiO_2$), tantalum pentoxide ($Ta_2O_5$) and niobium pentoxide ($Nb_2O_5$).

The electrolyte solution is adjusted according to the nature of the solution being measured.

The reference electrode 21 is advantageously of platinized platinum. The reference cell 2 also has a reservoir 32 filled with the electrolyte solution and a reference pump 31 to pump the electrolyte solution from the reservoir 32 to the tank 20. The tank 20 is of a suitable material, for example alloys based on zirconium Zr, titanium Ti, tantalum Ta or niobium Nb previously oxidized under air in a furnace between 500° C. and 600° C. for at least forty-eight hours.

The measuring cell 4 also has a measuring electrode 41, advantageously of platinized platinum. This measuring electrode 41 is to be immersed in the solution being measured. The measuring cell 4 also has a reservoir 52 filled with the solution being measured and a pump 51 to pump the solution from the reservoir 52 into a container 40 in which the measuring electrode 41 and the tank 20 are immersed. Container 40 can also be of an alloy based on zirconium Zr, titanium Ti, tantalum Ta or niobium Nb or any other suitable metal material, from the point of view of corrosion, for the solution being measured.

The reference electrodes 21 and the measuring electrodes 41 play the role of potentiometers 22 and 42 to respectively measure a reference electric potential $E_R$ of the reference solution in the tank 20 and a measurement electric potential $E_M$ of the solution being measured in the container 40. These electrodes 21 and 41 are made of platinized platinum, also called platinum black, which is a microporous platinum. Microporous platinum enables to obtain potential measurements independent of the flow that occurs around the electrodes from a given flow.

In FIG. 3a it can be seen that when the electrode is simply made of platinum, there is a range where the measured potential depends on the flow of fluid around the electrode. In contrast, as FIG. 3b shows, when the electrode is made of platinized platinum, the measured potential, beyond a given flow, is constant.

The measuring device 1 also has a temperature regulator $R_T$ to ensure a roughly identical temperature in the tank 20 and the container 40.

The temperature regulator $R_T$ has a reference thermometer 23 immersed in the tank 20 filled with electrolytes, a measuring thermometer 43 to be placed in contact with the solution being measured in the container 40, and a temperature comparator 24. The temperature comparator 24 compares the temperatures $T_R$, $T_M$ measured by the reference and measuring thermometers 23, 43.

Thus, temperatures $T_R$ and $T_M$ are directly measured.

The thermometer 23, or 43, and the electrodes 21 or 41, respectively, can together form single element (see FIG. 2). In this case, the electrode 21 or 41 is formed by a sheath 211, 411 of platinum closed at its end 211e, 411e in an airtight manner and electrochemically coated at this end with platinum black 212, 412. An industrial platinum resistance thermometer 213, 413 is positioned inside the sheath 211, 411. Thus, a single part has a double function: measuring temperature and potential.

The temperature regulator $R_T$ also has at least one heater 25, 45 controlled by the temperature comparator 24 to heat the reference cell 2 or the measuring cell 4 according to the result of the comparison made by the temperature comparator 24.

The heater may be composed of two furnaces: a first furnace 25 surrounding the reference cell 2 and a second furnace 45 surrounding the container 40 filled with the solution being measured in which the measuring electrode 41 is immersed.

In this latter case, the temperature comparator 24 controls the first furnace 25. Another temperature comparator 44 is provided and compares temperature $T_M$ measured by the measuring thermometer 43 to a set temperature $T_C$. This temperature comparator 44 controls the furnace 45 surrounding the container 40 filled with the solution, enabling to control the temperature prevailing in the solution being measured so that it is roughly equal to the set temperature $T_C$. Indirectly, via the temperature comparator 24, this also enables to control the temperature $T_R$ of the tank 20 so that it is roughly equal to the temperature $T_M$ of the solution and therefore to the set temperature $T_C$.

The measuring device 1 also has an inlet 36 for hydrogen gas into the tank 20 of the reference cell 2 and an inlet 56 for hydrogen gas into the solution being measured. In the case of the reference cell, the inlet 36 is possibly connected through an electrolyte solution reservoir 32 on the side of tank 20. In the case of the measuring cell 4, the inlet 56 is possibly connected to a reservoir for the solution being measured 52 within the measuring cell 2.

The measuring device 1 also has a partial pressure regulator $R_{PP}$ to ensure a roughly identical hydrogen partial pressure on the side of the reference cell 2 and the measuring cell 4, in the reservoirs 32 and 52, if applicable.

The partial pressure regulator $R_{PP}$ may have a valve 35, 55 positioned on each of hydrogen gas inlets 36, 56 so as to open when the hydrogen partial pressure on the side of the tank 20, respectively the solution being measured, is below a set partial pressure $P_{H,C}$.

The partial pressure regulator $R_{PP}$ also has a comparator 34, 54, for each of valves 35, 55. The comparator 34 compares the partial hydrogen pressure $P_{H,R}$ on the side of the tank 20 to the set partial pressure $P_{H,C}$ and controls the opening of the valve 35 according to the result of the comparison. At the same time, the comparator 54 compares the partial hydrogen pressure $P_{H,M}$ on the side of the solution to the set partial pressure $P_{H,C}$ and controls the opening of valve 55 according to the result of the comparison.

If the partial hydrogen pressure $P_{H,R}$ or $P_{H,M}$ is less than the set partial pressure $P_{H,C}$, the corresponding comparator 34, 54 opens the corresponding valve 35, 55 (if it is closed) or increases its opening (if the valve is gradual and not binary). In the opposite case, the comparator 34 or 54 closes valve 35 or 55 so as to cut off the inflow of hydrogen into the electrolyte solution reservoir 32 or the solution being measured reservoir 52, or decreases the opening of the valve 35 or 55 to limit the inflow of hydrogen.

In a variant illustrated by FIG. 4, the partial pressure comparator $R_{PP}$ may be a pipe-liquid column assembly connecting the headspace of the reservoirs 32 and 52, respectively of the electrolyte solution and the solution being measured. The hydrogen is injected directly into both reservoirs 32, 52 by pipes 36 and 56 immersed in the respective solutions contained in the reservoirs 32 and 52.

Gas outlets 37 and 57 are also provided, for example in the form of pipes of which one end arrives at the headspace of the respective reservoirs 32 and 52. The other end of these pipelines is directed toward a liquid column CL ensuring the same pressure (by means of an identical liquid height) in both reservoirs 32 and 52.

The measuring device 1 also has a fluid pressure regulator $R_{PF}$ to ensure a roughly identical fluid pressure in the tank 20 and the container 40.

The fluid pressure regulator $R_{PF}$ may have a reference manometer 62, a measuring manometer 64, an outlet valve 61 connected to the tank 20 and a fluid pressure comparator 63 to compare the fluid pressure of the tank 20 to that of the solution being measured and to consequently control the outlet valve 61 connected to the tank 20. A same pressure in the tank 20 and the container 40 cancels a parasitic electric potential called "flow potential" induced by a liquid flow between the tank 20 and the container 40 through the sintered filter 201.

The reference manometer 62 measures pressure $P_R$ at the outlet of the reference pump 31 and the measuring manometer 64 measures the pressure $P_M$ at the outlet of the pump 51 of the measuring cell 4. If the pressure $P_R$ is greater than pressure $P_M$ then the fluid pressure comparator 63 controls the opening of the outlet valve 61 linked to the tank 20, this cause a pressure drop in the tank 20. In the contrary case, the fluid pressure comparator 63 controls the closing of the outlet valve 61, leading to increased pressure in the tank 20 following the continuous injection of the reference solution by the reference pump 31.

The fluid pressure regulator $R_{PF}$ may also have a pressure comparator 65 to compare the pressure $P_M$ measured at the outlet of pump 51 of the measuring cell 4 to a set pressure $P_C$. This pressure comparator 65 controls the pump 51 of the measuring cell 4 according to the result of the comparison. Thus, if the measured pressure $P_M$ is less than the set pressure $P_C$, the pressure comparator 65 controls the increase in pumping power of the pump 51 of the measuring cell 4. In the opposite case, the pressure comparator 65 controls the pump 51 of the measuring cell 4 to decrease its pumping power.

Generally, the fluid pressure regulator $R_{PF}$ ensures a same pressure inside the tank 20 and the container 40 to cancel a fluid flow between the tank 20 and the container 40.

Thus, in a variant, the pressure comparator 63 can control the reference pump 31 and the pressure comparator 65 an outlet valve 46 connected to container 40 to control the evacuation of the solution being measured from container 40.

In another variant, the fluid pressure comparator 63 and the pressure comparator 65 respectively control the outlet valves 61, 46 connected to the tank 20 and the container 40.

In yet another variant, the fluid pressure comparator 63 and the pressure comparator 65 respectively control the pumps 31, 51 of the reference cell 2 and the measuring cell 4. It will be noted that in the measuring device 1 such as described above, there are two independent circulation circuits, one for the reference cell 2 and the other for the measuring cell 4. Thus, chemical contaminations of one by the other are prevented.

By means of the materials used, and notably the use of two hydrogen electrodes, the measuring device 1 is not limited to use in the temperature range of liquid water, i.e., between 0° C. and 370° C. when the pressure in the tank 20 and/or the reservoir 40 is greater than the saturation pressure at the temperature considered. For example, at 300° C., the saturation vapor pressure of water is around 86 bars. The pH measuring device can therefore work for pressures above 86 bars. Furthermore, the solution can be either dilute or concentrated, which allows using measuring devices 1 in coolant circuits of conventional or nuclear power stations, for production of electricity in pressurized water reactors and boiling water reactors or for naval propulsion.

Ionic strength $\sigma_R$ of the reference solution of the tank 20 is adapted to ionic strength $\sigma_M$ of the solution being measured of the container 40 by adding salt dissolved in the solution being measured, such as sodium chloride NaCl or sodium nitrate $NaNO_3$, for example.

Figure 5:
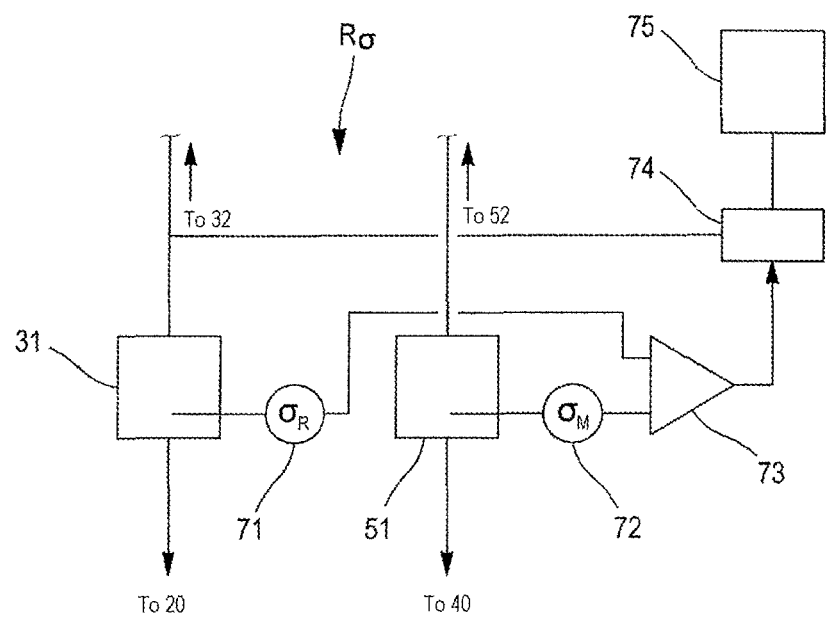
FIG. 5 shows one example of embodiment of an ionic strength regulator used in the measuring device of FIG. 1.

For this, an ionic strength regulator $R_\sigma$, illustrated in FIG. 5, usable with the measuring device 1 described above, has ionic strength sensors 71, 72 respectively for measuring ionic strengths $\sigma_R$, $\sigma_M$ of the reference solution and solution being measured upstream of the reference cell 2 and the measuring cell 4, an ionic strength comparator 73 and a pump 74 linked to a reservoir 75 containing a mixture of solution and salt.

For example, the ionic strength sensors 71 and 72 are positioned directly in the reference solution reservoir 32 and the solution being measured reservoir 52.

Advantageously, in order to allow a counter-reaction loop with injection of a mixture of solution and salt, the ionic strength sensors 71 and 72 may even be placed between the tank 20 and the pump 31 of the reference cell 2 on one hand, and between the container 40 and the pump 51 of the measuring cell 4 on the other hand.

Even more advantageously, in order to enable both a counter-reaction loop with injection of a mixture of solution and salt and to avoid areas of high pressure, the ionic strength sensors 71 and 72 can be placed between the reference reservoir 32 and the pump 31 of the reference cell 2 on one hand, and between the measuring reservoir 52 and the pump 51 of the measuring cell 4 on the other hand.

The ionic strength sensors 71 and 72 may be conductivity meters, such as, for example, platinized platinum wires that are electrically isolated from the metal components of measuring device 1.

Ionic strengths $\sigma_R$, $\sigma_M$ are then compared by the ionic strength comparator 73 whose outlet controls the pump 74 according to the result of the comparison.

In a first variant (illustrated in FIG. 5), the pump 74 of the ionic strength regulator $R_\sigma$ can be positioned between the reservoir 75 of mixture of the solution with the salt and the solution being measured, for example between the reservoir 32 and the pump 31 of the reference cell 2, to bring the mixture of the solution (which is the reference solution) with the salt of the reservoir 75 to the reference solution.

In the case where ionic strength $\sigma_R$ in the reference solution is less than ionic strength $\sigma_M$ in the solution being measured, the pump 74 is activated. Otherwise, water must be injected into the too-concentrated reference solution.

In another variant, the pump 74 of ionic strength regulator $R_\sigma$ can be positioned between the reservoir 75 of mixture of the solution (which is the solution being measured) with the salt and the solution being measured, for example between the reservoir 52 and the pump 51 of the measuring cell 4, to bring the mixture of the solution with the salt of the reservoir 75 to the solution being measured.

Moreover, the reference solution is prepared so as to initially have a reference solution with an ionic strength greater than that of the solution to be measured and to inject the quantity of salt only into the solution being measured to bring the ionic strength value of the solution being measured to that of the ionic strength of the reference solution.

In the case where ionic strength $\sigma_M$ in the solution being measured is less than ionic strength $\sigma_R$ in the reference solution, the pump 74 is activated.

Operating Principle:

By means of measuring device 1, the potential difference between the reference potential $E_R$ measured by the reference electrode 21 and the measurement potential $E_M$ measured by the measuring electrode 41 can be measured and therefore, it is possible to know the potential difference between the solution in the tank 20 and the solution being measured for which it is wished to know the pH.

The battery formed by the measuring device 1 is:

$$Pt_R|H_{2(g)}/H^+_{(aq)}::H^+_{(aq)}/H_{2(aq)}|Pt_M.$$

Generally, potential difference $\Delta E$ is given by the following relationship:

$$\Delta E = \frac{RT_M}{F}\ln\frac{a_{H^+_{(aq,M)}}}{\sqrt{\frac{p_{H_2,M}}{p^0}}} - \frac{RT_R}{F}\ln\frac{a_{H^+_{(aq,R)}}}{\sqrt{\frac{p_{H_2,R}}{p^0}}} + E_j;$$

with R=8,314 472 J·mol⁻¹·K⁻¹, the ideal gas constant; F=9.65·10⁴ C·mol⁻¹, the Faraday constant; $a_{H+(aq,M)}$ the hydrogen ion activity in the solution being measured; $a_{H+(aq,R)}$ the hydrogen activity in the tank 20; $p_{H2,M}$ the partial pressure (more precisely fugacity) of hydrogen $H_2$ in the solution being measured in the container 40; $p_{H2,R}$ the partial pressure (more precisely fugacity) of hydrogen $H_2$ in the reference solution in the tank 20; $p^0=1$ bar, the standard pressure; $E_j$ the junction potential in the sintered filter 201. The junction potential $E_j$ is not measurable and depends on deviations in temperature, pressure, concentration, ionic strength and flow between the tank 20 and the container 40.

Given that the temperature regulator $R_T$ keeps temperatures $T_M$ and $T_R$ equal, the preceding relationship is simplified:

$$\Delta E = \frac{RT}{F}\ln\frac{a_{H^+_{(aq,M)}}}{a_{H^+_{(aq,R)}}} \cdot \sqrt{\frac{p_{H_2,R}}{p_{H_2,M}}} + E_j;$$

with T the common value of temperatures $T_M$ and $T_R$.

Partial pressure regulator $R_{PP}$ keeps the partial hydrogen pressures in the tank 20 and the solution being measured equal. The following simplified relationship is then obtained:

$$\Delta E = \frac{RT}{F}\ln\frac{a_{H^+_{(aq,M)}}}{a_{H^+_{(aq,R)}}} \cdot + E_j;$$

that is $$pH_M = pH_R - \frac{F(\Delta E - E_j)}{RT\ln(10)};$$

with 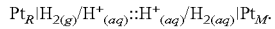 the pH of the solution being measured and $pH_R = -\log a_{H^+_{(aq,R)}}$, the pH of the electrolyte solution.

Although the junction potential Ej cannot be measured, the proposed measuring device 1 minimizes it by cancellation of temperature deviations (by means of temperature regulator $R_T$), pressure deviations (by means of fluid pressure regulator $R_{PF}$) and ionic strength deviations (by addition of salt into the reference solution and solution being measured.)

The invention claimed is:

1. A pH measuring device (1) comprising:
a) a reference cell including:
a tank filled with an electrolyte solution;
a platinized platinum reference electrode immersed in the tank; and
a first circulation circuit extending through the tank;
b) a measuring cell including:
a platinized platinum measuring electrode to be immersed in the solution being measured; and
a second circulation circuit independent from the first circulation circuit extending from the circulation of the reference cell configured so that cross chemical contamination is prevented;
c) a temperature regulator configured to maintain the same temperature in the reference cell and the measuring cell;
d) a partial pressure regulator configured to maintain the same hydrogen partial pressure in the reference cell and the measuring cell, wherein the partial pressure regulator is configured to independently control the partial pressure in each cell; and
e) a fluid pressure regulator configured to maintain the same pressure in the reference cell and the measuring cell, wherein the fluid pressure regulator is configured to independently control the fluid pressure in each cell.

2. Measuring device according to claim 1, in which the temperature regulator has a reference thermometer immersed in the electrolyte solution, a measuring thermometer to be placed in contact with the solution being measured, and a temperature comparator to compare the temperatures measured by the reference and measuring thermometers.

3. Measuring device according to claim 2, in which the temperature regulator also has at least one heater to heat the electrolyte solution or solution being measured according to the result of the comparison performed by the temperature comparator.

4. Measuring device according to claim 1, also comprising an inlet for hydrogen gas into the electrolyte solution and an inlet for hydrogen gas into the solution being measured.

5. Measuring device according to claim 4, in which the partial pressure regulator has a valve positioned on each of the hydrogen gas inlets so as to open when the hydrogen partial pressure in the electrolyte solution, respectively the solution being measured, is below a set partial pressure.

6. Measuring device according to claim 5, in which the partial pressure regulator also has a comparator, for each of the valves, to compare the hydrogen partial pressure in the electrolyte solution, respectively the solution being measured, to the set partial pressure and to control the opening of the corresponding valve, according to the result of the comparison.

7. Measuring device (1) according to claim 1, wherein the fluid pressure regulator has a reference manometer, a measuring manometer, an outlet valve, and a fluid pressure comparator, wherein the reference manometer and the measuring manometer are connected to the inputs of the fluid pressure comparator, and the output of the fluid pressure comparator is connected to the outlet valve.

8. Measuring device according to claim 1, also comprising an ionic strength regulator configured to maintain the same ionic strength in the reference cell and the measuring cell.

* * * * *